(12) United States Patent
Rice et al.

(10) Patent No.: US 7,629,573 B2
(45) Date of Patent: Dec. 8, 2009

(54) TISSUE PHANTOM CALIBRATION DEVICE FOR LOW LEVEL LIGHT IMAGING SYSTEMS

(75) Inventors: Bradley W. Rice, Danville, CA (US); David G. Nilson, Walnut Creek, CA (US); Normand P. Nantel, San Leandro, CA (US); Tamara L. Troy, San Francisco, CA (US)

(73) Assignee: Xenogen Corporation, Alameda, CA (US)

( * ) Notice: Subject to any disclaimer, the term of this patent is extended or adjusted under 35 U.S.C. 154(b) by 1353 days.

(21) Appl. No.: 10/997,324

(22) Filed: Nov. 24, 2004

(65) Prior Publication Data

US 2005/0145786 A1    Jul. 7, 2005

(51) Int. Cl.
  *G01D 18/00*  (2006.01)
  *C12M 1/00*  (2006.01)
  *A61B 6/00*  (2006.01)

(52) U.S. Cl. .............. 250/252.1; 600/477; 600/478; 435/288.7

(58) Field of Classification Search ............... 348/187, 348/77, 129, 68, 216.1; 382/110, 128, 133; 250/252.1; 600/476–478; 424/9.6, 9.8; 356/72, 244, 317, 402, 425, 433, 229, 230
See application file for complete search history.

(56) References Cited

U.S. PATENT DOCUMENTS

| | | | |
|---|---|---|---|
| 4,196,994 | A | 4/1980 | de Jesus et al. |
| 4,727,247 | A | 2/1988 | Johnston |
| 4,948,975 | A | 8/1990 | Erwin et al. |
| 5,008,548 | A | 4/1991 | Gat |
| 5,060,061 | A | 10/1991 | Shishido et al. |
| RE33,973 | E | 6/1992 | Kriz et al. |
| 5,130,794 | A | 7/1992 | Ritchey |
| 5,202,091 | A | 4/1993 | Lisenbee .............. 422/52 |
| 5,227,627 | A | 7/1993 | Gamarnik et al. |

(Continued)

FOREIGN PATENT DOCUMENTS

EP    0 228 877    7/1987

(Continued)

OTHER PUBLICATIONS

Office Action dated Jun. 30, 2009 in U.S. Appl. No. 11/682,710.

(Continued)

*Primary Examiner*—Victor R Kostak
(74) *Attorney, Agent, or Firm*—Beyer Law Group LLP

(57) ABSTRACT

The present invention relates to a phantom device that simplifies usage and testing of a low intensity light imaging system. The phantom device includes a body and a light source internal to the body. The body comprises an optically selective material designed to at least partially resemble the optical behavior of mammalian tissue. Imaging the light source or phantom device may incorporate known properties of the optically selective material. Testing methods described herein assess the performance of a low-level light imaging system (such as the software) by processing light output by the phantom device and comparing the output against known results. The assessment builds a digital representation of the light source or test device and compares one or more components of the digital representation against one or more known properties for the light source or the test device.

47 Claims, 8 Drawing Sheets

U.S. PATENT DOCUMENTS

| | | | |
|---|---|---|---|
| 5,272,518 A | 12/1993 | Vincent | |
| 5,319,209 A | 6/1994 | Miyakawa et al. | 250/459.1 |
| 5,376,803 A * | 12/1994 | Mc Fee et al. | 250/496.1 |
| 5,414,258 A | 5/1995 | Liang | 250/252.1 |
| 5,515,161 A | 5/1996 | Blumenfeld | |
| 5,587,583 A | 12/1996 | Chin et al. | |
| 5,636,299 A | 6/1997 | Bueno et al. | 385/15 |
| 5,637,874 A | 6/1997 | Honzawa et al. | 250/361 C |
| 5,650,135 A | 7/1997 | Contag et al. | 424/9.1 |
| 5,672,881 A | 9/1997 | Striepeke et al. | 250/461.2 |
| 5,689,110 A | 11/1997 | Dietz et al. | |
| 5,705,807 A | 1/1998 | Throngnumchai et al. | 250/214 P |
| 5,738,101 A | 4/1998 | Sappey | 128/665 |
| 5,796,477 A * | 8/1998 | Teich et al. | 356/318 |
| 5,840,572 A | 11/1998 | Copeland et al. | 435/286.7 |
| 5,865,754 A * | 2/1999 | Sevick-Muraca et al. | 600/476 |
| 5,867,250 A | 2/1999 | Baron | 351/212 |
| 5,883,830 A | 3/1999 | Hirt et al. | |
| 5,970,164 A | 10/1999 | Bamberger et al. | 382/128 |
| 6,205,244 B1 | 3/2001 | Bawolek et al. | |
| 6,217,847 B1 | 4/2001 | Contag et al. | 424/9.1 |
| 6,242,743 B1 | 6/2001 | DeVito et al. | 250/363.05 |
| 6,321,111 B1 | 11/2001 | Perelman et al. | 600/477 |
| 6,364,829 B1 | 4/2002 | Fulghum | 600/160 |
| 6,381,058 B2 | 4/2002 | Ramm | |
| 6,597,439 B1 | 7/2003 | Hakamata | |
| 6,615,063 B1 | 9/2003 | Ntziachristos et al. | 600/312 |
| 6,642,953 B1 | 11/2003 | Velasco et al. | |
| 6,759,814 B2 | 7/2004 | Vogel et al. | |
| 6,775,567 B2 | 8/2004 | Cable et al. | 600/407 |
| 6,919,919 B2 | 7/2005 | Nelson et al. | |
| 6,922,246 B2 | 7/2005 | Nilson | |
| 7,116,354 B2 | 10/2006 | Rice et al. | |
| 7,129,464 B2 * | 10/2006 | Buchin | 250/214 VT |
| 7,151,252 B2 * | 12/2006 | Lehmann et al. | 250/252.1 |
| 7,331,673 B2 | 2/2008 | Ono | |
| 7,352,840 B1 * | 4/2008 | Nagarkar et al. | 378/19 |
| 7,482,167 B2 | 1/2009 | Sammak et al. | |
| 2001/0028510 A1 | 10/2001 | Ramm et al. | |
| 2002/0072677 A1 * | 6/2002 | Sevick-Muraca et al. | 600/473 |
| 2003/0036860 A1 | 2/2003 | Rice et al. | |
| 2003/0156194 A1 | 8/2003 | Sugiura et al. | |
| 2005/0077459 A1 | 4/2005 | Engler et al. | |
| 2005/0145786 A1 | 7/2005 | Rice et al. | |
| 2006/0081770 A1 * | 4/2006 | Buchin | 250/214 VT |
| 2007/0013780 A1 | 1/2007 | Rice et al. | |

FOREIGN PATENT DOCUMENTS

| | | |
|---|---|---|
| EP | 0 491 131 | 6/1992 |
| EP | 0656731 | 6/1995 |
| FR | 2 802 009 | 6/2001 |
| WO | WO 94/00742 | 1/1994 |
| WO | WO 00/17643 | 3/2000 |

OTHER PUBLICATIONS

Office Action dated Jun. 24, 2009 in U.S. Appl. No. 11/523,480.
Office action dated Jan. 8, 2009 in U.S. Appl. No. 11/523,480.
Office action dated Dec. 29, 2008 in U.S. Appl. No. 11/682,710.
International Search Report dated May 28, 2009 in PCT Application No. PCT/US08/55965.
Written Opinion dated May 28, 2009 in PCT Application No. PCT/US08/55965.
Summons to Attend Oral Proceedings dated May 8, 2009 for European Application No. 02742268.2.
Integrated Photomatrix Limited, "Closed Loop Control", Dorset, England, available Dec. 1, 2001.
Dynex Technologies, Inc., website, A Thermo BioAnalysis Company "Dynex Microplates", http://www.dynextechnologies.com/index.html, printed Apr. 19, 2002.
Optronic Labroatories, Inc., website, Manufacturer of Light Measurement Instrumentation, Standards, http://olinet.com/, printed Apr. 19, 2002.
Labsphere, website http://labsphere.com, printed Apr. 19, 2002.
Lambda Research Corporation,website, http://lambdares.com , printed Apr. 19, 2002.
Hamamatsu Corporation, USA, website, http://usa.hamamatusu.com/ pp. 1-4, Apr. 27, 2001, printed on Apr. 27, 2001.
Hamamatsu, Imaging Box Instruction Manual, 55310-224-1, Nov. 2000.
Mahmood, U. et al., "Near-Infrared Optical Imaging of Protease Activity for Tumor Detection", Radiology 1999, 213, pp. 866-870.
Weissleder, R. et al., "Shedding Light onto Live Molecular Targets", Nature Medicine, Jan. 2003, vol. 9, No. 1, pp. 123-128.
Prahl, Scott. "Optical Phantoms," http://omlc.ogi.edu/classroom/phantom/index.html, 1998, printed Jul. 18, 2007.
Vernon, Marcia L. et al., "Fabrication and characterization of a solid polyurethane phantom for optical imaging through scattering media," Applied Optics, vol. 38, No. 19, Jul. 1, 1999, pp. 4247-4251.
European Search Report dated Feb. 5, 2008 from EP Application No. 02742268.2 (5 pages).

* cited by examiner

TISSUE PHANTOM CALIBRATION DEVICE FOR LOW LEVEL LIGHT IMAGING SYSTEMS

CROSS-REFERENCE TO RELATED APPLICATION

This application claims priority under 35 U.S.C. §120 from U.S. patent application Ser. No. 10/068,573, filed Feb. 6, 2002 and titled "Light Calibration Device for Use in Low Level Light Imaging Systems," which is incorporated herein by reference for all purposes.

FIELD OF THE INVENTION

The present invention generally relates to low-level light imaging systems. More specifically, the present invention relates to tissue phantom calibration devices for use in low-level light imaging systems.

BACKGROUND OF THE INVENTION

One new type of imaging involves the capture of low intensity light—on the order of $10^3$-$10^{10}$ photons/sec/cm$^2$/steradian—from a biological sample. A source of the light indicates a portion of the sample where an activity of interest may be taking place. In one example, the sample is a small animal such as a mouse and the light source could be tumor cells labeled with light emitting reporters such as firefly luciferase or fluorescent proteins or dyes. This technology is known as in vivo optical imaging.

Detection of light-emitting probes in-vivo within small living animals relies on the semitransparent nature of mammalian tissue, and requires complex instrumentation such as a high-sensitivity low-noise camera and advanced imaging software tools to interpret an image. The propagation of light through tissue is a diffusive process and therefore depends on the scattering and absorption properties of tissue. Advanced computer codes can localize a source of light in three-dimensions in tissue by simulating the photon diffusion process. This technique is often referred to as diffuse luminescent imaging tomography. Testing and development of such software often employs a living specimen, such as a real mouse, to verify accurate software results. In addition, purchasers of an imaging system often train new users on the system and/or software to build user familiarity. However, a living mouse is not an ideal subject for these instances. Careful handling requirements and the need for anesthesia make living mammals non-ideal for software development, software testing, and personnel training.

In view of the foregoing, the development of non-living models of light sources in tissue-like phantom materials would be desirable.

SUMMARY OF THE INVENTION

The present invention relates to a phantom device that simplifies usage, testing, and development of low-level light imaging systems. The phantom device includes a body and a light source internal to the body. The internal light source emits light, such as luminescent light or fluorescent light. The body comprises an optically selective material designed to at least partially resemble the optical behavior of mammalian tissue. The body shape may resemble a real animal (e.g., in shape, topography, and/or height). Imaging the light source or phantom device may incorporate known properties of the optically selective material. Testing methods described herein assess the performance of a low-level light imaging system (such as 3D reconstruction of diffuse tomography software) by processing light output by the phantom device and comparing the output against known results for the phantom device. The assessment builds a digital representation of the light source or phantom device and compares one or more components of the digital representation against one or more known properties for the light source or the test device.

In one aspect, the present invention relates to a phantom device for use with a low-level light imaging system. The device comprises a body including one or more surfaces and an optically selective material designed to at least partially resemble the optical behavior of mammalian tissue. The device also comprises a low intensity light source disposed within the body and configured to emit light from within the body, through the optically selective material and to the one or more surfaces. The light source is configured to emit photon flux in the range of about $10^4$ to about $10^{13}$ photons/second.

In another aspect, the present invention relates to a device for testing a low-level light imaging system. The device comprises a body including one or more surfaces and a substantially homogeneous and optically selective material designed to at least partially resemble the optical behavior of mammalian tissue. The body includes a shape that resembles a mammal and a height for the body that is designed to resemble a height of a mammal to be imaged. The device also comprises a low intensity light source disposed within the body.

In yet another aspect, the present invention relates to a method for testing a low-level light imaging system. The method comprises capturing an image of at least a portion of a phantom device disposed in a field of view for a camera included in the low-level light imaging system. The phantom device comprises a body including an optically selective material designed to at least partially resemble the optical behavior of mammalian tissue. The method also comprises building a digital representation of a light source internal to the phantom device using data included in the image. The method further comprises comparing a component of the digital representation to a known property for the light source or the phantom device.

In still another aspect, the present invention relates to a computer readable medium including instructions for testing a low-level light imaging system. The instructions comprise instructions for capturing an image of at least a portion of a phantom device disposed in a field of view for a camera included in the low-level light imaging system. The phantom device comprises a body including an optically selective material designed to at least partially resemble the optical behavior of mammalian tissue. The instructions also comprise instructions for reconstructing a digital representation of the light source internal to the phantom device using data included in the image. The instructions further comprise instructions for comparing a component of the digital representation to a known property for the light source or the phantom device.

These and other features of the present invention will be described in more detail below in the detailed description of the invention and in conjunction with the following figures.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION OF THE PREFERRED EMBODIMENTS

In the following detailed description of the present invention, numerous specific embodiments are set forth in order to provide a thorough understanding of the invention. However, as will be apparent to those skilled in the art, the present invention may be practiced without these specific details or by using alternate elements or processes. In other instances well known processes, components, and designs have not been described in detail so as not to unnecessarily obscure aspects of the present invention.

Figure 1A:
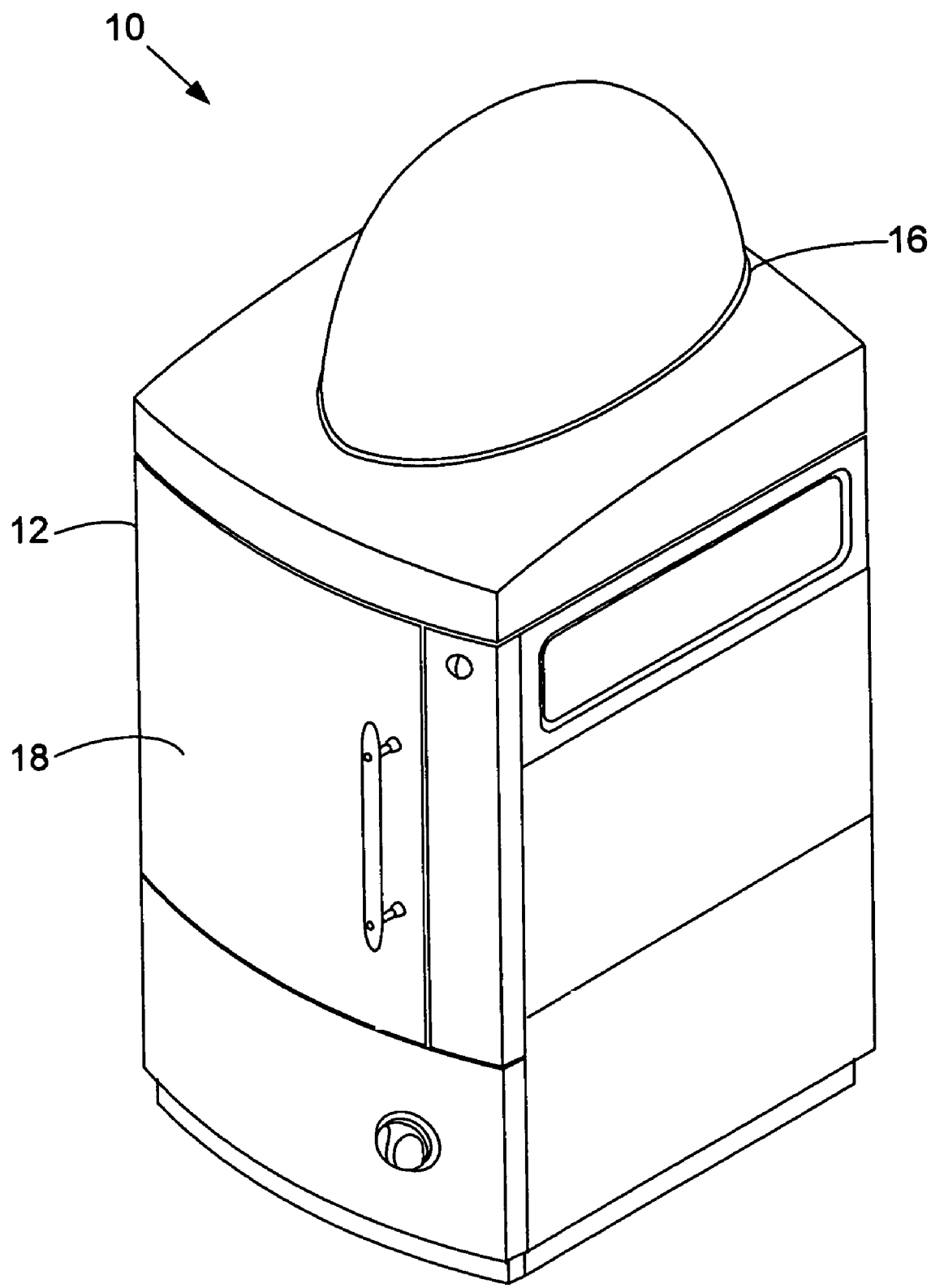
FIGS. 1A and 1B illustrate a perspective view of an imaging system in accordance with one embodiment of the present invention.
Figure 1B:
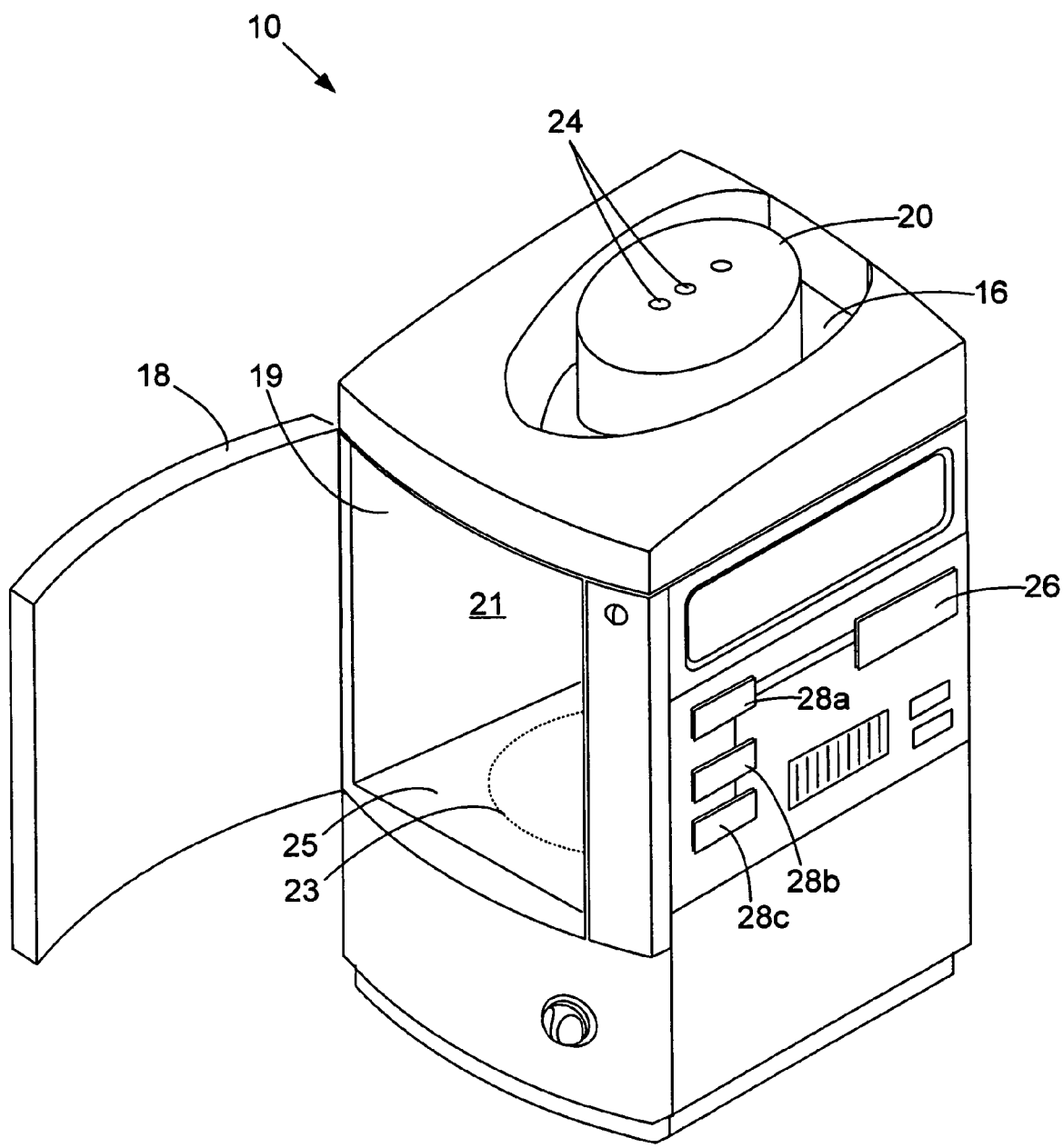

The present invention relates to tissue phantom devices for use in an imaging system that captures an image of a low intensity light source. Tissue phantoms are inanimate devices that simulate the diffusion of photons through mammalian tissue. When imaged, a light source within the tissue phantom device often causes the device—or portions thereof—to glow or emit light from a surface, hence the term 'phantom'. As the term is used herein, 'test device', 'phantom device' and 'tissue phantom' are used interchangeably and all relate to a device used in an imaging system that includes an internal light source. A phantom device permits, for example, benchmarking of diffuse tomographic imaging systems and software. FIGS. 1A and 1B illustrate an imaging system 10 configured to capture photographic, luminescence and fluorescent images in accordance with one embodiment of the present invention.

Imaging system 10 may be used for imaging a low intensity light source, such as luminescence from luciferase-expressing cells, fluorescence from fluorescing molecules, and the like. The low intensity light source may be included in any of a variety of living or non-living light-emitting samples. Non-living light-emitting samples may include calibration devices and phantom devices as described herein. Living light-emitting samples may include, for example, animals or plants containing light-emitting molecules, tissue culture plates containing living organisms, and multi-well plates (including 96, 384 and 864 well plates) containing living organisms. Animals may include any mammal, such as a mouse or rat containing luciferase-expressing cells.

System 10 finds wide use in imaging and research. The ability to track light-emitting cells in a small laboratory animal such as a mouse or rat opens up a wide range of applications in pharmaceutical and toxilogical research. These include in vivo monitoring of infectious diseases, tumor growth in metastases, transgene expression, compound toxicity, and viral infection or delivery systems for gene therapy. The ability to detect signals in real-time and in living animals means that the progression of a disease or biological process can be studied throughout an experiment with the same set of animals without a need to sacrifice for each data point. This results in higher-quality data using fewer animals and speeds the process of screening compounds leading to more rapid drug discovery.

Imaging system 10 comprises an imaging box 12 having a door 18 and inner walls 19 (FIG. 1B) that define an interior cavity 21 that is adapted to receive a light-emitting sample or phantom device in which low intensity light is to be detected. Imaging box 12 is suitable for imaging including the capture of low intensity light on the order of individual photons, for example. Imaging box 12 is often referred to as "light-tight". That is, box 12 seals out essentially all of the external light from the ambient room from entering the box 12, and may include one or more seals that prevent light passage into the box when door 18 is closed. In a specific embodiment, door 18 comprises one or more light-tight features such as a double baffle seal, while the remainder of chamber 12 is configured to minimize any penetration of light into cavity 21.

Phantom devices as described below are placed within box 12 for imaging by opening door 18, inserting the testing device in chamber 21, and closing door 18. One suitable imaging system is the IVIS-200 as provided by Xenogen corporation from Alameda, Calif. Further description of a suitable imaging box 12 is provided in commonly owned pending patent application Ser. No. 09/905,668 entitled "3-D Imaging Apparatus for In-Vivo Representations", which is incorporated by reference herein in its entirety for all purposes. Although imaging system 10 is shown with a single cabinet design, other embodiments of the present invention include a disparate imaging box 12 and computer that includes processing system 28 and a dedicated display.

Imaging box 12 includes an upper housing 16 adapted to receive a camera 20 (FIG. 1B). A high sensitivity camera 20, e.g., an intensified or a charge-coupled device (CCD) camera, is mounted on top of upper housing 16 and positioned above imaging box 12. CCD camera 20 is capable of capturing luminescent, fluorescent, structured light and photographic (i.e., reflection based images) images of a living sample or phantom device placed within imaging box 12. One suitable camera includes a Spectral Instruments 620. Series as provided by Spectral Instruments of Tucson, Ariz. CCD camera 20 is cooled by a suitable source such as a refrigeration device that cycles a cryogenic fluid to cool the CCD camera via conduits that communicate the cooling fluid into channels 24. A suitable refrigeration device comprises the "CRYOTIGER" compressor, which can be obtained from IGC-APD Cryogenics Inc., Allentown, Pa. Other methods, such as liquid nitrogen, may be used to cool camera 20.

Imaging system 10 may also comprise a lens (not shown) that collects light from the specimen or phantom device and provides the light to the camera 20. A stage 25 forms the bottom floor of imaging chamber 21 and includes motors and controls that allow stage 25 to move up and down to vary the field of view 23 for camera 20. A multiple position filter wheel may also be-provided to enable spectral imaging capability.

Imaging box 12 may also include one or more light emitting diodes on the top portion of chamber 21 to illuminate a sample during photographic image capture. Other features may include a gas anesthesia system and heated sample shelf to maintain an animal's body temperature during image capture and anesthesia.

FIG. 1B shows system 10 with the removal of a side panel for imaging box 12 to illustrate various electronics and processing components included in system 10. Imaging system 10 comprises image processing unit 26 and processing system 28. Image processing unit 26 optionally interfaces between camera 20 and processing system 28 and may assist with image data collection and video data processing. Processing system 28, which may be of any suitable type, comprises hardware including a processor 28a and one or more memory components such as random-access memory (RAM) 28b and read-only memory (ROM) 28c.

Processor 28a (also referred to as a central processing unit, or CPU) couples to storage devices including memory 28b and 28c. ROM 28c serves to transfer data and instructions uni-directionally to the CPU, while RAM 28b typically transfers data and instructions in a bi-directional manner. A fixed disk is also coupled bi-directionally to processor 28a; it provides additional data storage capacity and may also include any of the computer-readable media described below. The fixed disk may be used to store software, programs, imaging data and the like and is typically a secondary storage medium (such as a hard disk).

Processor 28a communicates with various components in imaging box 12. To provide communication with, and control of, one or more system 10 components, processing system 28 employs software stored in memory 28c that is configured to permit communication with and/or control of components in imaging box 12. For example, processing system 28 may include hardware and software configured to control camera 20. The processing hardware and software may include an I/O card, control logic for controlling camera 20. Components controlled by computer 28 may also include motors responsible for camera 20 focus, motors responsible for position control of a platform supporting the sample, a motor responsible for position control of a filter lens, f-stop, etc.

Processing system 28 may also interface with an external visual display (such as computer monitor) and input devices such as a keyboard and mouse. A graphical user interface that facilitates user interaction with imaging system 10 may also be stored on system 28, output on the visual display and receive user input from the keyboard and mouse. The graphical user interface allows a user to view imaging results and also acts an interface to control the imaging system 10. One suitable imaging software includes "LivingImage" as provided by Xenogen Corporation of Alameda, Calif.

Processing system 28 may comprise software, hardware or a combination thereof. System 28 may also include additional imaging hardware and software, test and calibration software, and image processing logic and instructions for processing information obtained by camera 20. For example, stored instructions run by processor 28a may include instructions for i) receiving image data corresponding to light emitted from a phantom device as described herein, ii) building a point, 2-D or 3-D digital representation of a light source internal to the phantom device using data included in the image, and iii) comparing a component of the digital representation to a known property for the light source or the test device.

Imaging system 10 employs a quantitative model that estimates the diffusion of photons in tissue. In one embodiment, the model processes in vivo image data and in order to spatially resolve a 3D representation of the size, shape, and location of the light emitting source. Typically, the tomographic model is stored as instructions in memory of processing system 28. Various diffusion and reconstruction models may be implemented by system 10 to represent photon propagation through a mammalian subject or a phantom device described herein. One suitable tomographic example of software that builds a digital representation of a light source internal to a mammalian sample or phantom device using data from one or more images is described in commonly owned and pending patent application Ser. No. 10/606,976 entitled "Method and Apparatus for 3-D Imaging of Internal Light Sources" and naming Brad Rice et al. as inventors. This application is incorporated by reference herein and its entirety for all purposes.

Figure 2A:
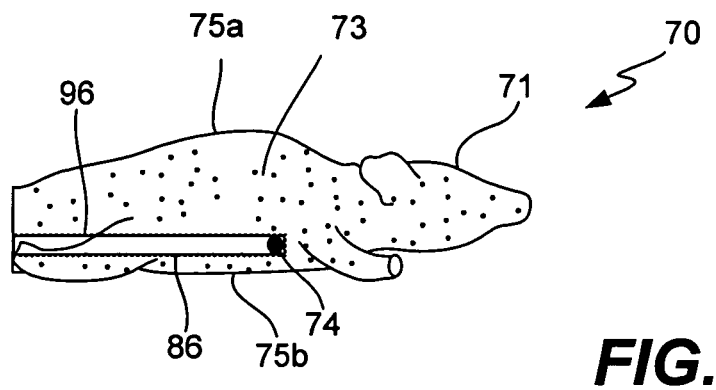
FIGS. 2A-2C illustrate different views of a phantom device in accordance with one embodiment of the present invention.
Figure 2B:
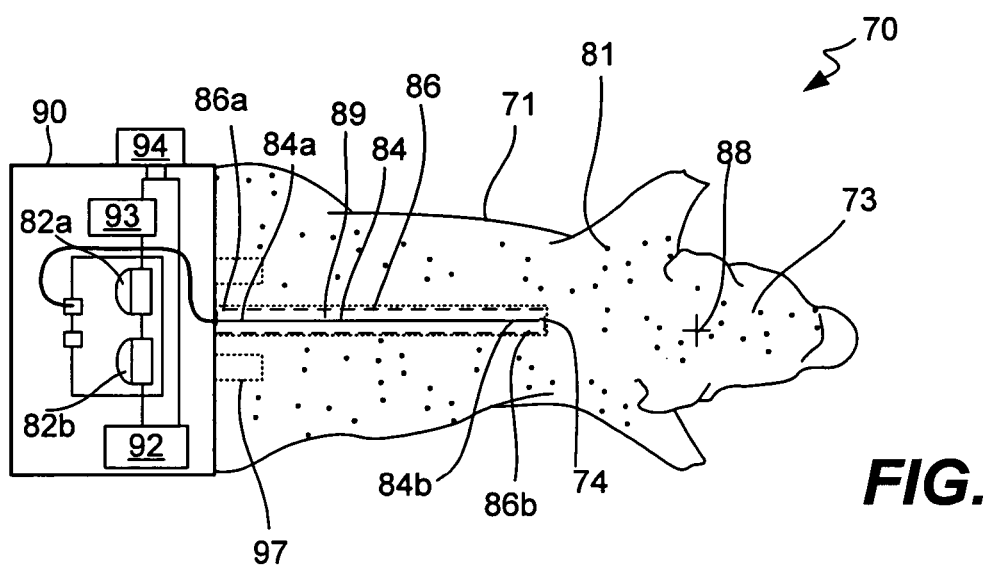
Figure 2C:
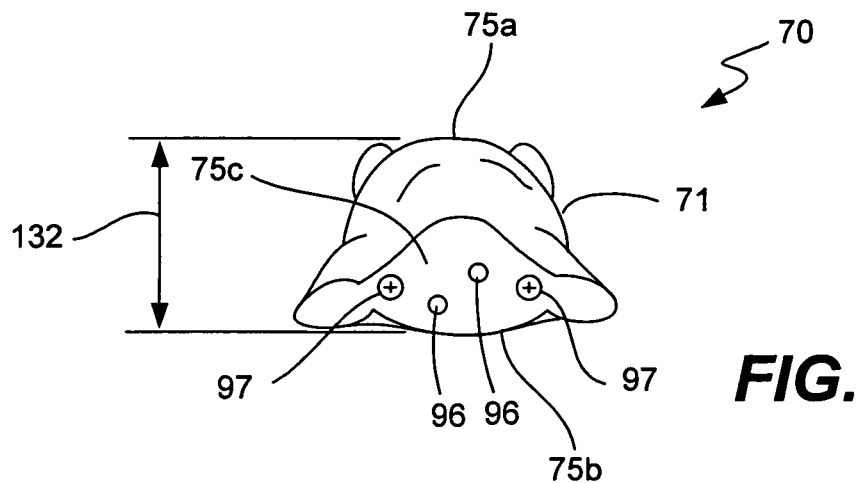

The present invention employs a phantom device to assist testing, validation and benchmarking of software implemented by system 10. The phantom device has other applications with a low level light imaging system, as will be described below. FIGS. 2A-2C illustrate different views of a phantom device 70 in accordance with one embodiment of the present invention. Phantom device 70 simulates the diffusion of photons through mammalian tissue. Phantom device 70 is well suited for benchmarking of diffuse tomographic imaging systems and software. Phantom device 70 comprises a body 71 and a low intensity light source 74 disposed within body 71.

Body 71 includes an optically selective material 73 and one or more surfaces 75. Optically selective material 73 is designed to at least partially resemble the optical behavior of mammalian tissue. Mammalian tissue acts as a turbid medium that both scatters and absorbs photons.

Optically selective material 73 is designed or configured to resemble an optical absorption property of mammalian tissue. Tissue absorption in living mammals is generally affected by the presence of hemoglobin, which absorbs light significantly in the blue-green region of the visible spectrum and is relatively transparent in the red at wavelengths greater than 600 nanometers. In one embodiment, the optically selective material 73 comprises a polyurethane base with a reddish dye that absorbs light significantly in the blue-green region and is relatively transparent in a red region of the visible spectrum. One dye suitable for use with the present invention comprises Disperse Red 1 as provided by Sigma-Aldrich of St. Louis, Mo. In one embodiment, a dye solution consisting of 124 mg of disperse red dye to 91 ml ethyl alcohol is mixed. The ratio of dye solution to polyurethane is from about 0.001 ml/gm to about 0.02 ml/gm. In a specific embodiment, the ratio of dye solution to polyurethane is about 0.0104 ml/gm. It is understood that different dyes and different amounts of a particular dye may be used with a polymer to achieve a desired absorption level.

In one embodiment, spectral absorption characteristics of mammalian tissue in the visible spectrum are used to determine how optically selective material 73 is dyed at multiple wavelength points in the visible spectrum. FIG. 2E illustrates an exemplary absorption coefficient curve 202 for different wavelengths in the visible spectrum. Absorption curve 206 approximates the absorption performance of mammalian tissue. Individual points 204 on curve 202 represent coefficients of absorption at a specific wavelength. Material 73 is dyed to resemble optical absorption characteristics of mammalian tissue in the visible wavelength range. Absorption coefficient curve 202 corresponds to the absorption characteristics of optically selective material 73. Each point 204 is stored in memory and applied during reconstruction of an internal light source for an image taken of phantom device 70 at a corresponding wavelength. Image capture and light source reconstruction at different wavelengths may then proceed with known absorption characteristics of material 73 at each wavelength. Absorption coefficient curve 202 thus allows spectral imaging at multiple wavelengths that resembles varying spectral absorption characteristics of mammalian tissue across the visible spectrum.

Optically selective material 73 is also designed and configured to resemble an optical scattering property of mammalian tissue. For wavelengths greater than 600 nanometers, the scattering coefficient mammalian tissue is about 20 $cm^{-1}$, corresponding to an effective length for scattering of about 0.05 cm. In a regime where scattering is pronounced, a significant amount of light can escape the tissue of a living mammal but the emission is often highly diffuse. In a specific embodiment, optically selective material 73 comprises one or more scattering particles 81 to resemble the optical scattering of mammalian tissue. The type of scattering particle and amount disposed within material 73 may be varied according to a desired degree of scattering within phantom device 70. Many particles will not be visible to the human eye. One suitable scattering particle comprises titanium dioxide ($TiO_2$), for example, which is added to a polymer precursor before polymerization to subsequently form material 73 and a polymer body for phantom device 70. In one embodiment, the ratio of titanium dioxide beads to polyurethane is from about 0.002 gm/gm to about 0.003 gm/gm. In a specific embodiment, the ratio of titanium dioxide beads to polyurethane is about 0.0026 gm/gm.

The amount of titanium oxide added to the precursor may be tailored according to optical scattering property of mammalian tissue. Similar to spectral absorption, the optical scattering characteristics of mammalian tissue in the visible spectrum may also be used to determine how optically selective material 73 is particulated at multiple wavelength points in the visible spectrum. Typically, scattering decreases with increasing wavelength in the visible spectrum for mammalian tissue. Material 73 then includes optical scattering characteristics that decrease and mimic mammalian tissue in the visible wavelength range.

Figure 2D:
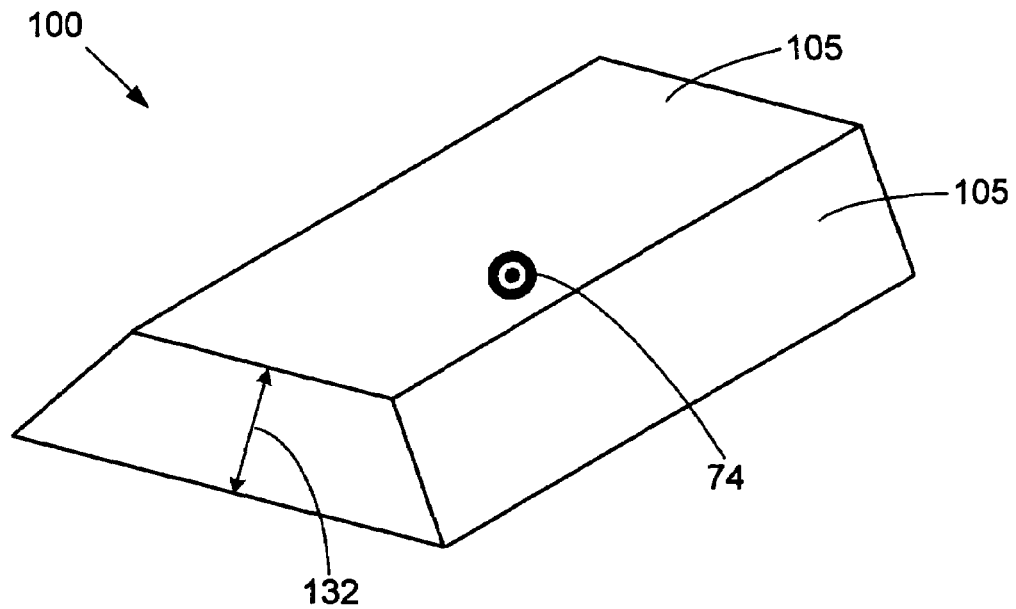
FIG. 2D illustrates a testing device that includes a trapezoidal shape in accordance with a specific embodiment of the present invention.
Figure 2G:
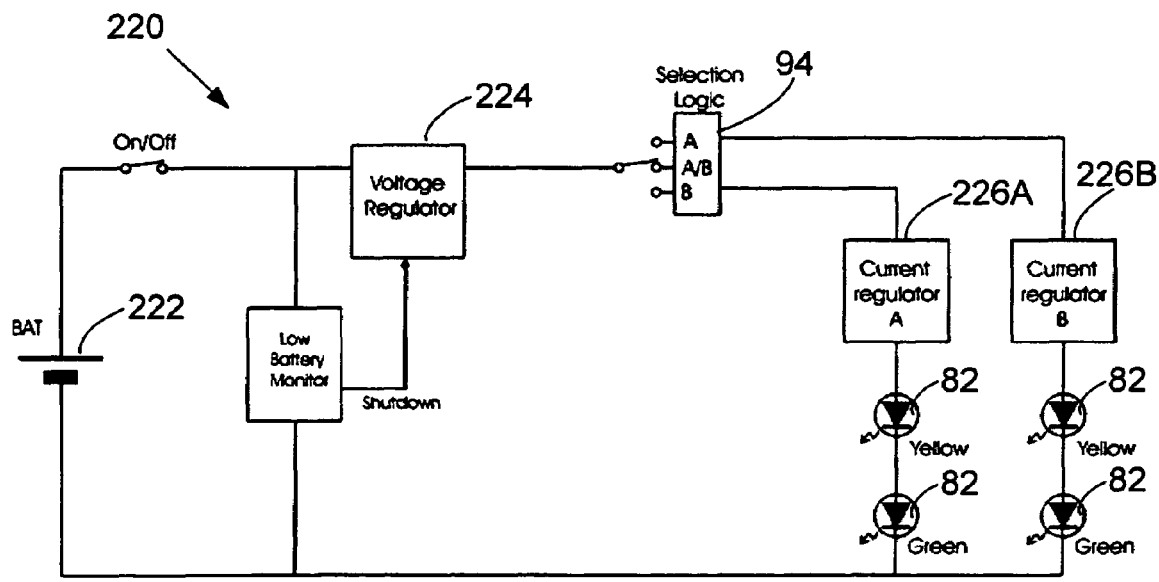
FIG. 2G illustrates an exemplary circuit for generating light with LED light supplies in accordance with a specific embodiment of the present invention.
Figure 2E:
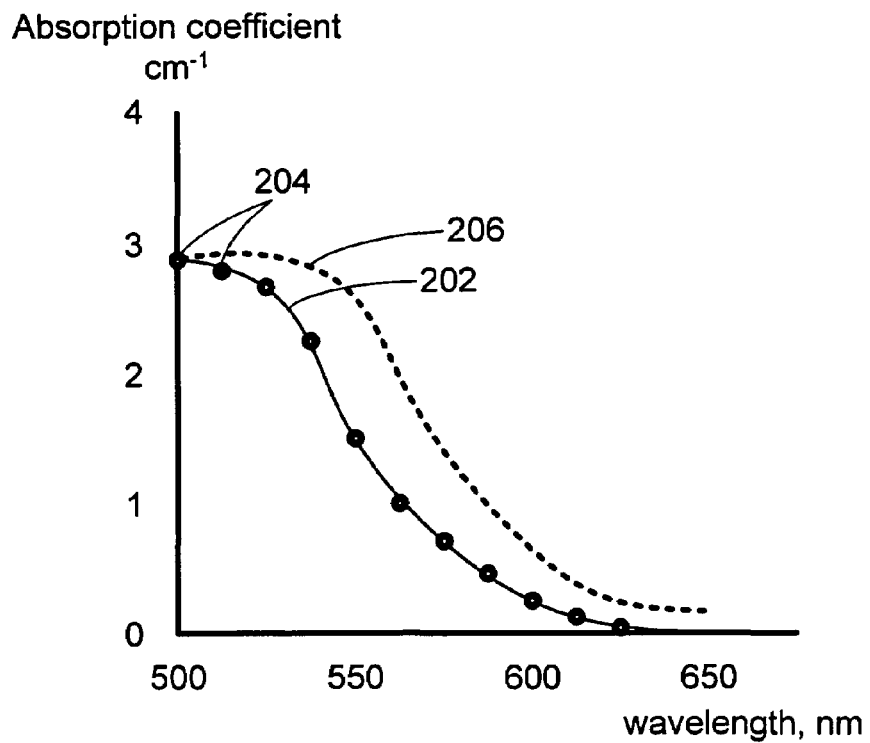
FIG. 2E illustrates an exemplary absorption coefficient curve for different wavelengths in accordance with a specific embodiment of the present invention.
Figure 2F:
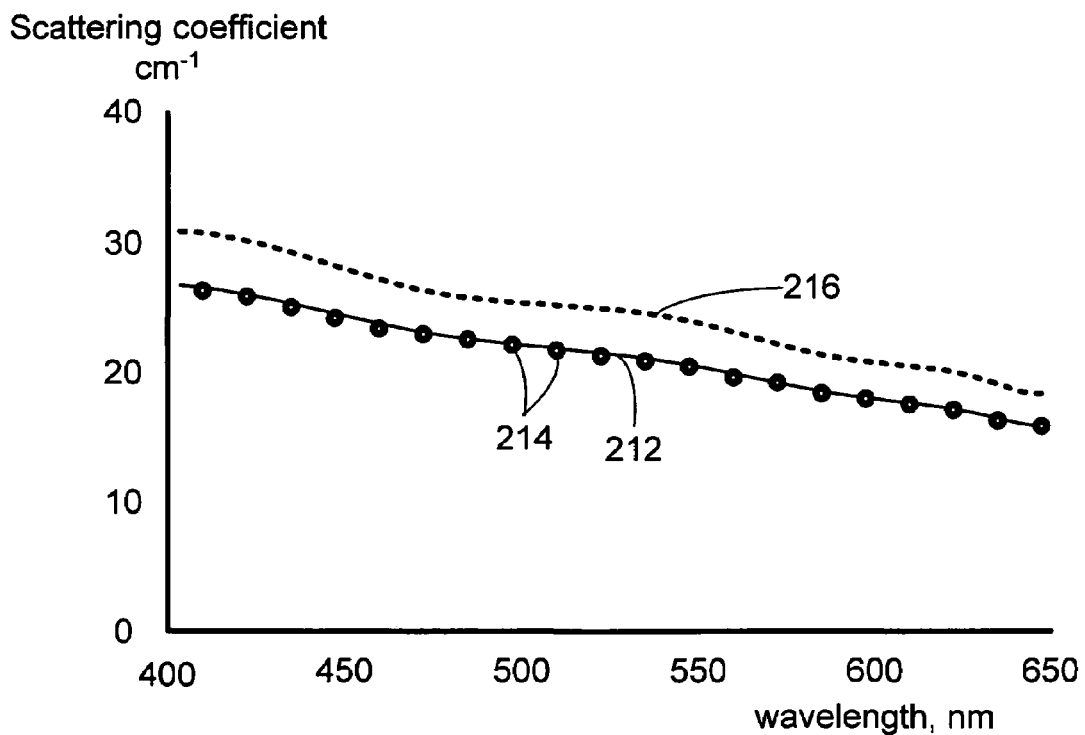
FIG. 2F illustrates an exemplary scattering coefficient curve for different wavelengths in accordance with a specific embodiment-of the present invention.

FIG. 2F illustrates a representative scattering coefficient curve 212 stored in memory for different wavelengths in the visible spectrum. Scattering coefficient curve 216 approximates the scattering performance of mammalian tissue. Individual points 214 on curve 212 represent coefficients of optical scattering at a specific wavelength. Material 73 is particulated to resemble optical scattering characteristics of mammalian tissue in the visible wavelength range according to curve 212. Image capture and light source reconstruction at different wavelengths may then proceed with known optical scattering characteristics of material 73 at each wavelength. Each point 214 is stored in memory and applied during reconstruction of an internal light source for an image taken of phantom device 70 with a corresponding wavelength. Scattering curve 202 thus allows spectral imaging at multiple wavelengths that resembles varying spectral scattering characteristics of mammalian tissue across the visible spectrum.

In FIG. 2A, body 71 also provides mechanical integrity for device 70 and protects optical and electronic components contained therein. In this case, material 72 used in body 71 includes a suitable rigidity to resist forces associated with usage, such as handling. In a specific embodiment, body 71 comprises polyurethane alloyed to obtain one or more optical properties.

In one embodiment, optically selective material 73 is substantially homogeneous. It is understood that real animals are not homogeneous and that tissue absorption for living mammals varies with the type of tissue or tissue cells, and is generally affected by varying particles and quantities such as the presence of hemoglobin. However, software run by imaging system 10 may implement homogeneous assumptions on the optical behavior of mammalian tissue when imaging a living mouse. The software may also implement the same homogeneous assumptions when imaging phantom device 70 and optically selective material 73. To facilitate testing of software configured with such assumptions, optically selective material 73 may then comprise a substantially homogeneous composition. This may be achieved during manufacture of body 71 by mixing polymer precursors and optical additives inserted therein to achieve consistency throughout the precursor before polymerization. In addition, polymerization of the precursor may be controlled to minimize the formation of voids and other optical impurities in body 71.

In another embodiment, body 71 is heterogeneous and includes at least two different materials. This may include heterogeneous phantom devices not manufactured to achieve homogeneous composition and/or phantom devices constructed from multiple parts having different optical properties. For example, body may include a) an upper portion of device 70 that is constructed to diffuse and scatter light as described for material 73 and b) a non-optically selective lower portion. When the device 70 is imaged using a camera disposed above the device, the non-optically selective lower portion may not greatly affect device imaging. Body 71 may also include parts attached thereto that also create a heterogeneous structure. For example, the back side of body 71 may be opaque and house various electrical components. Alternatively, rods 86 may comprise a material different from body 71 that creates a heterogeneous structure. Other heterogeneous configurations and inclusions are contemplated.

Body 71 includes one or more surfaces 75. The number of surfaces 75 will depend on the configuration of phantom device 70. Frequently, phantom device 70 comprises a bottom surface 75*b* that is substantially flat and allows phantom device to be readily rested on a flat surface. The number and shape of other surfaces will depend on the shape chosen for phantom device 70. In one embodiment, phantom device 70 resembles a mammal. For FIGS. 2A-2C, body 71 comprises a shape that resembles a mouse with distal portions for the arms and legs omitted. In this case, casting a polymer precursor in a mold dimensioned to resemble a mouse may form test device 70 and define all surfaces 75. The surfaces may then include a surface topography that is designed to match the surface topography of a mammal commonly imaged.

The test device 100 of FIG. 2D comprises a trapezoidal geometry in accordance with a specific embodiment of the present invention. In this case, testing device 100 comprises six surfaces 105 shaped to form an extended frustum. Testing device 100 is machined to include surfaces 105 of known dimensions, which simplifies imaging and measuring surface topography for device 100. In this case, verification of software using phantom device 100 may rely on known dimensions for each surface of testing device 100. In another embodiment, test device includes a surface shape that resembles a cylinder.

Height 132 is defined as the distance from the bottom surface 75*b* to the topmost surface 75*a* (FIGS. 2C and 2D). In one embodiment, height 132 is configured relative to the depth of field of focus of an imaging system that phantom device 70 is used with. Alternately, height 132 may be designed to resemble the height of a mammal to be imaged. It is understood that the depth of field of focus for an imaging system will vary depending on several parameters, and vary with the type of imaging performed in the system (e.g., camera characteristics and continual imaging of the top surface of a mammalian specimen is then dependent on the mammal); and the height 132 of phantom device 70 may be tailored accordingly. A test device having a height between about 10 mm to about 40 mm is suitable for many imaging systems. In a specific embodiment, height 132 is about 20 mm, which corresponds to the average height of a mammalian specimen commonly used in imaging applications.

Phantom device 70 may also include a fiducial mark 88 that serves as a spatial reference when imaging phantom device 70. Thus, software implemented by imaging system 10 may compare the reconstructed location of light source 74 relative to fiducial mark 88 with the known location light source 74 relative to fiducial mark 88. In other embodiments, fiducial mark 88 is not included.

In one embodiment, phantom device 70 is constructed using conventional plastics fabrication techniques. Additional fabrication steps may be implemented to achieve one more properties custom to phantom device 70. For example, a vacuum pump may be used to withdraw and remove air bubbles from a polymer mixture during fabrication to further increase the homogeneous nature of body material 71. In addition, ultrasonic energy may be used to break up titanium dioxide beads into smaller particles than those commercially available and increase homogeneous composition of body material 71. In a specific embodiment, body material 71 is made according to the following procedure. Commercially available polyurethane precursors are obtained and separated into two parts: part A and part B. Ethyl alcohol is added to a dye powder and about 7.5 ml of the solution is mixed with about 70 g of polyurethane part B. About 1.95 g of titanium dioxide beads are added to the solution and stirred. The solution is then placed into an ultrasonic cleaner with about 1 quart of water as a cleaner. Ultrasonic energy is then applied for about seven to eight minutes to break up the titanium dioxide, avoid formation of any clumps, and provide uniformly distributed mixture. About 274 g of polyurethane part B are then added and the mixture is stirred. About 100 g of polyurethane part A is added to about 85 g of the mixture previously developed, and the combination is again stirred. The preformed polymer is then placed in a vacuum for about 15 to about 60 seconds to withdraw and remove air bubbles from a polymer mixture. The preformed polymer is then poured into a suitably shaped mold and cured under pressure. In one embodiment, a mouse shaped mold is obtained by freezing a dead mouse to create a detailed dimension mold.

Low intensity light source 74 emits low-intensity light within phantom device 70. The light then travels through optically selective material 73 to one or more surfaces of device 70. In one embodiment, a low intensity light source of the present invention emits light within device 70 in the range of about $10^4$ to about $10^{13}$ photons/second. For some imaging systems, a low intensity light source 74 that emits flux in the range of about $10^4$ to about $10^{10}$ photons/second is suitable. Other light fluxes are permissible with the present invention. Photons/second is one unit of measure suitable to quantify the amount of light produced by light source 74. Other units of measure are known to one of skill in the art, such as Watts. For reference, the conversion of photons/second to Watts is 3.3 nanowatts equals about $10^{10}$ photons/second at 600 nm. In one embodiment, light source 74 emits light between about $10^{-15}$ to $10^{-6}$ watts of light. The amount of light produced by light source 74 refers to the light emitted within body 71—not necessarily the amount of light generated by a light source (such as an LED) that initially generates the light. As will be described in further detail below, light source 74 may comprise multiple electronics and light transmission components that generate and cooperatively emit a desired intensity and/or spectrum of light within body 71.

Low intensity light source 74 may also be designed and configured to produce a desired-radiance from the surface of phantom device 70. Photons/second/centimeter squared/steradian are units of photon radiance on a surface. These units are used herein for convenience since they allow low-level lights to be characterized despite the size of the light source 74. A desirable range for light emitted from light source 74 will depend on a number of factors such as the sensitivity and saturation of the camera used, the ability of the imaging box to seal light, level of internally generated light in the imaging box, imaging system parameters such as integration time, binning, and f-stop, etc. In one embodiment, a low intensity light source of the present invention emits light within device 70 in the range of about $10^3$ to about $10^{11}$ photons/second/centimeter squared/steradian. For some imaging systems, a low intensity light source 74 that emits light in the range of about $10^9$ to about $10^{10}$ photons/second/centimeter squared/steradian is suitable. In some cases, the intensity of light emitted from light source 74 may be determined according to the sensitivity of a camera used in the imaging system over a duration corresponding to saturation of the camera caused by light emitted from the light source 74. Saturation refers to the amount of light and time it takes for the camera, or the analog-to-digital converter associated with the camera, to reach its exposure capacity. For example, the saturation duration may range from about five seconds to about five minutes, depending on the rate of light emitted from the object. For phantom device 70, the output of low intensity light source 74 may be increased to expedite imaging when imaging occurs over an extended period of time.

Suitable levels of illumination from low intensity light source 74 may also be described in terms of output power. In a specific embodiment, light source 74 emits from about $10^{-15}$ to about $10^{-6}$ watts of light. This range relatively compares to the intensity light provided by a tumor within a small mammal.

Light source 74 may also be configured to emit light in a wavelength range that resembles light used in imaging in a living animal subject. In a specific embodiment, light source 74 emits light that resembles the spectral characteristics of luciferase. In this case, assessment using phantom device 70 also permits spectral differences in absorbance of optically selective material 73 to help determine the location of light source 74 within body 71.

Figure 2H:
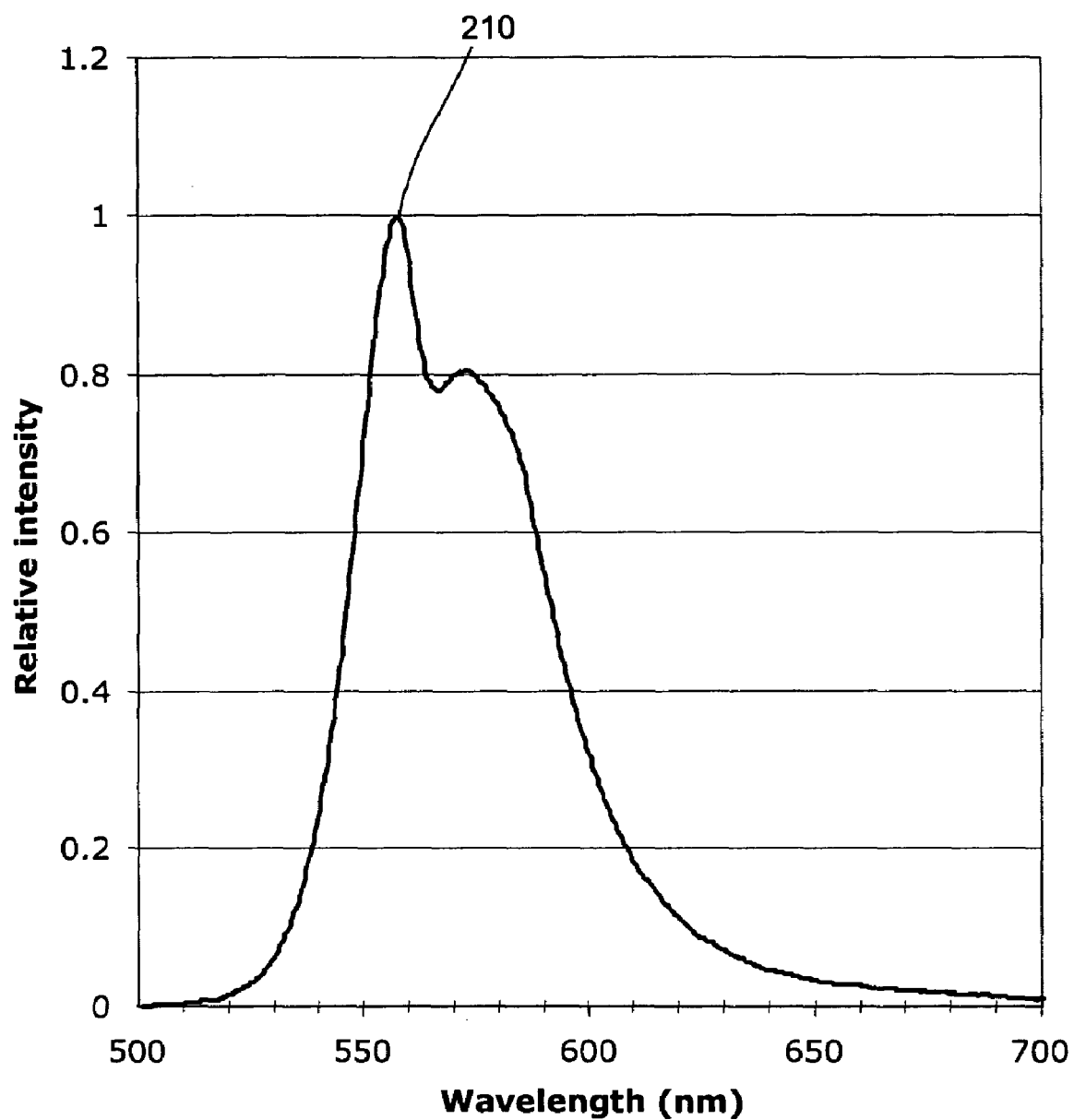
FIG. 2H illustrates an exemplary spectral output for a phantom device in accordance with a specific embodiment of the present invention.

Light source 74 and the optically selective material 73 may also be designed to produce a combined spectral output for device 70. FIG. 2H illustrates an exemplary spectral output 210 for phantom device 70 in accordance with a specific embodiment of the present invention. Devices of the present invention may include other spectral outputs. In general, light sources of the present invention may emit light in the range of about 400 nanometers to about 1300 nanometers. Within this range, light source 74 and optically selective material 73 may be configured or combined to emit light from device 70 according to any spectral curve or spectral output.

FIG. 2A illustrates phantom device 70 with an internal radiation light source 74 in accordance with one embodiment of the present invention. The radiation light source 74 comprises a radiation source that produces electrons and is configured to strike a light-emitting surface. Tritium is ($H_3$) is a radioactive form of Hydrogen gas ($H_2$) that continuously emits low energy Beta radiation (electrons). High pressure tritium gas or solid pellets may be sealed inside a small borosilicate glass vial or tube. Electrons released by the tritium impact a phosphor coating on the inside of the tube, which in turn emits a visible glow. The light-emitting surface then includes the glass wall and phosphor coating disposed thereon. Electrons emitted by the tritium excite the phosphor and create a low level light without filaments, heat dissipation and need for a battery and external power. One suitable radiation light source is a round traser GTLS lightsource provided by Traser Systems-mb-microtec of Niederwangen, Switzerland (www.mbmicrotec.com).

In one embodiment, the radiation light source is embedded at an end of a rod 86 that is inserted into a central volumetric portion of body 71. As shown in FIG. 2C, phantom device 70 comprises a hole 96 that receives rod 86. Hole 96 and rod 86 are dimensioned such that rod 86 a) press fits into hole 96 to minimize escape of light along the interface between rod 86 and hole 96 and b) hole 96 and rod 86 permit manual removal and insertion of rod 86 within hole 96. Rod 86 thus permits mechanical insertion and removal of radiation light source 74 deep within body 71. In one embodiment, rod 86 comprises the same optically selective material as phantom device 70. This reduces optical effects of rod 86 when imaging device 70 and maintains the homogeneous optical nature of body 71. When the optically selective material comprises a plastic or polyurethane base, this allows rod 86 and channel 89 to be machined to press fit dimensions to further reduce light escape along an interface between rod 86 and hole 96.

Device may comprise any number of internal light sources. FIGS. 2A and 2B illustrate one light source 74 and hole 96. FIG. 2C illustrates two holes 96. Three or more light sources are also suitable. Multiple holes included in body 71 allow multiple light sources 74 to be employed. A device may also use light sources than it has holes when there are multiple holes. In this case, a plug (a plastic cylinder that press fits into hole 96) made from optically selective material 73 may also be inserted into a hole when body 71 includes multiple holes and not all the holes are currently used.

In another embodiment, phantom device 70 emits fluorescent light and is intended for fluorescent light reconstruction with an imaging system that is configured to perform fluorescent analysis. In this case, a fluorophore is embedded in the end of rod 86 that is inserted into a central volumetric portion of body 71. One suitable fluorophore is indocyanide green, for example.

FIG. 2B illustrates a phantom device 70 with a light source 74 that employs light-emitting diode (LED) light supplies 82a and 82b in accordance with another embodiment of the present invention. Diode light supplies 82a and 82b generate light.

LED light supplies 82a and 82b are housed in electronics box 90. Box 90 attaches to a back surface 75c of phantom device 70 using two screws that mate with threaded inserts 97 disposed in body 71. Box 90 contains portable electronics components suitable to generate light. More specifically, box 90 comprises LED light supplies 82, battery 92, current regulating electronics 93, and a switch 94. Battery 92 provides power for LED light supply 82. In one embodiment, battery 92 is rechargeable, such as any of those commercially available from a wide array of vendors. Switch 94 allows a user to turn LED light supply 82 on/off.

Device 70 may include electrical components to facilitate substantially consistent light output from light supplies 82. Supplies 82 receive current from a current regulation source 93 that controls the amount of current provided to each light supply 82. In a specific embodiment, light supplies 82 are self-monitoring in that the light supplies 82 are designed or configured to monitor the amount of light generated therefrom and adapt the amount of light to maintain substantially consistent light output. For example, output from a monitoring diode may be used to control the current flowing to the LED, in order to maintain a constant light level. Using self-monitoring light sources in this manner allows device 70 to accommodate minor fluctuations in temperature or voltage without sacrificing consistent light output by light source 74 within body 71.

In a specific embodiment, LED light supplies 82 are housed in an optical coupling box that also receives one or more optical fibers 84. The box may comprise a suitably stiff material (e.g., plastic or aluminum) with holes for each LED light supply 82 and optical fiber 84. A commercially available fiber optic coupling device may be used to couple each optical fiber 84 to a wall of the box. The holes may be arranged on the box walls such that the LED light supplies 82 oppose a receiving end of the optical fiber 84.

In one embodiment, light source 74 emits a light spectrum that resembles a biological reporter. One suitable biological reporter is luciferase, which emits light generally in the red to green range of the visible spectrum (roughly from about 530 nm to about 650 nm). To resemble luciferase, LED light supplies 82 include a green LED 82a and a yellow LED 82b for each optical fiber 84 and light source 74.

In general, LEDs 82 may be selected to produce any desired emission spectrum for an internal light source. Many LEDs produce an amount of light that will saturate a low-level light imaging system. In one embodiment, the present invention reduces intensity of light produced by an LED light supply 82 before emission within device 70. In a specific embodiment, light source 74 comprises a fiber optic cable 84 configured to receive light from LED light supply 82 and emit a portion of the light within body 71. One end of fiber-optic cable 84 is configured relatively close to LED light supplies 82. LED light supplies 82 are configured to illuminate and transmit light into a first end of fiber-optic cable 84. The tip—or opposite end—of fiber-optic cable 84 within body 71 represents the output for light source 74. More specifically, fiber optic cable 84 has a first end configured to receive light from the LED light supply 82 and a second end 84b within the body.

Inexpensive LEDs for a range of visible wavelengths are commercially available from a wide array of vendors. In one embodiment, LED light supplies 82 include a green LED 82a and a yellow LED 82b for each optical fiber 84 and light source 74. In a specific embodiment, LED light supplies 82 comprise a LED model nos. HLMPK640-FGN00 (green) and HLMP1440-HIB00 (yellow), which are both from Agilent Technologies of Palo Alto, Calif. In some cases, the LEDs are selected with a high power to overcome inefficient coupling between placing a single fiber optic cable in the vicinity between two adjacent LEDs 82. One or more filters may also be included to tailor the spectral supply to light source 74 to further resemble a light spectrum for a biological reporter.

FIG. 2B illustrates a simplified arrangement for coupling fiber-optic cable 84 to receive light from LED light supplies 82. In one embodiment, each LED light supply is configured to not shine light on the surface of body 71 that interfaces with box 90 (FIG. 2C). This avoids scattering light into body 71 at the interface that may detract from imaging light source 74. Fiber-optic cables 84 then receive light from light supplies 82 such that the light supplies 82 direct light away from body 71 and then cables 84 wind within box 90 and position for insertion into body 71.

Phantom device 70 includes a channel 89 configured to receive optical fiber 84. Channel 89 may be included in either hole 96 or rod 86. In the embodiment shown, channel 89 is disposed by cutting a groove along a surface of rod 86. Channel 89 is machined and sized to receive optical fiber 84. Rod 86 thus provides mechanical support for optical fiber 84 within phantom device 70. Rod 86 and channel 89 each extend from a first end 86a disposed proximate to the light supply to a second end 86b within the body. In one embodiment, rod 86 comprises the same optically selective material as phantom device 70. This reduces optical effects of rod 86 when imaging device 70.

Although phantom device 70 has been described with respect to a single hole 96 and light source 74, body 71 may comprise multiple holes 96. In this case, device 70 may then permit two light sources 74 (radiation, LED, fluorescent, or other) to be inserted into body 71 and imaged. In this case, box 90 includes circuitry to power additional light supplies 82, if needed, for the second light source 74. For device with multiple holes 96, holes 96 not in use may be plugged with a press fit rod 86 not including a light supply 74.

FIG. 2G illustrates an exemplary circuit 220 for generating light with. LED light supplies 82 in accordance with a specific embodiment of the present invention. One or more batteries 222 power the circuit. In a specific embodiment, two rechargeable 3.7V batteries 222, connected in series, yield a nominal output of 7.4V when fully charged. When the 2-position ON/OFF switch 94 is turned ON, a voltage regulator 224 receives the battery output and provides a constant 7.0 V to the LED drive circuitry. Voltage regulator 224 also monitors the state of batteries 222. When the battery voltage drops below 7.0V, voltage regulator 224 shuts itself down in order to prevent over-discharge of batteries 222, which may shorten their useful life. One suitable voltage regulator comprises a model no MAX882ESA as provided by Maxim-Dallas of Sunnyvale, Calif.

Circuit 220 includes two parallel LED pairs 82. A three-position selector switch 94 and logic determines which LED pair 82 will be turned on. More specifically, the three-position switch 94 allows current regulator A or B to be on while the other remains off, or both A and B to be on simultaneously. Each current regulator 226A provides a relatively stable current of 6.9 mA to its respective LED pair 82. Two LEDs 82 within a branch are in series and thus conduct a similar current. One suitable current regulator comprises a model no LM234Z-3 as provided by National Semiconductor of Santa Clara, Calif. To the extent the drive for current regulator 226 varies (+/−3%), light output from the green and yellow LEDs within that branch will remain in the same ratio. In addition, this will not affect the other branch.

In one embodiment, the present invention employs phantom device 70 to assess the performance of an imaging system. The assessment processes light output by the phantom device and compares a reconstruction of phantom device 70 and internal light source 74 against known and expected results. More specifically, the assessment builds a digital representation of the light source 74 and/or phantom device 70 and compares one or more components of the digital representation against one or more known properties for the light source or the phantom device. By taking an image of the phantom device 70—or a portion thereof—and comparing the processed result with a known or expected result, the accuracy of the imaging system and its software imaging characteristics may be assessed, verified, and adapted if necessary.

In addition, phantom device 70 finds wide use for a low-light level imaging system when the system is not employed for imaging a living mammal. For example, phantom device 70 may be used when training new users or new purchasers of an imaging system, such as individuals in a research lab. Phantom device 70 thus finds particular service when new users are learning how to use an imaging system and complications associated with handling a living mammal are beneficially avoided. Phantom device 70 may also be used to test hardware components in system 10 as required for routine calibration or verification of an imaging system. For example, components such as the camera, positioning system and lens may be routinely tested for health. In addition, phantom device 70 may be used upon system breakdown, such as when a filter may have cracked. In testing for diagnosis of an unknown breakdown, the imaging system comprises so many parts that use of a living mammal may be detrimental and test device 70 simplifies repeated testing.

Figure 3:
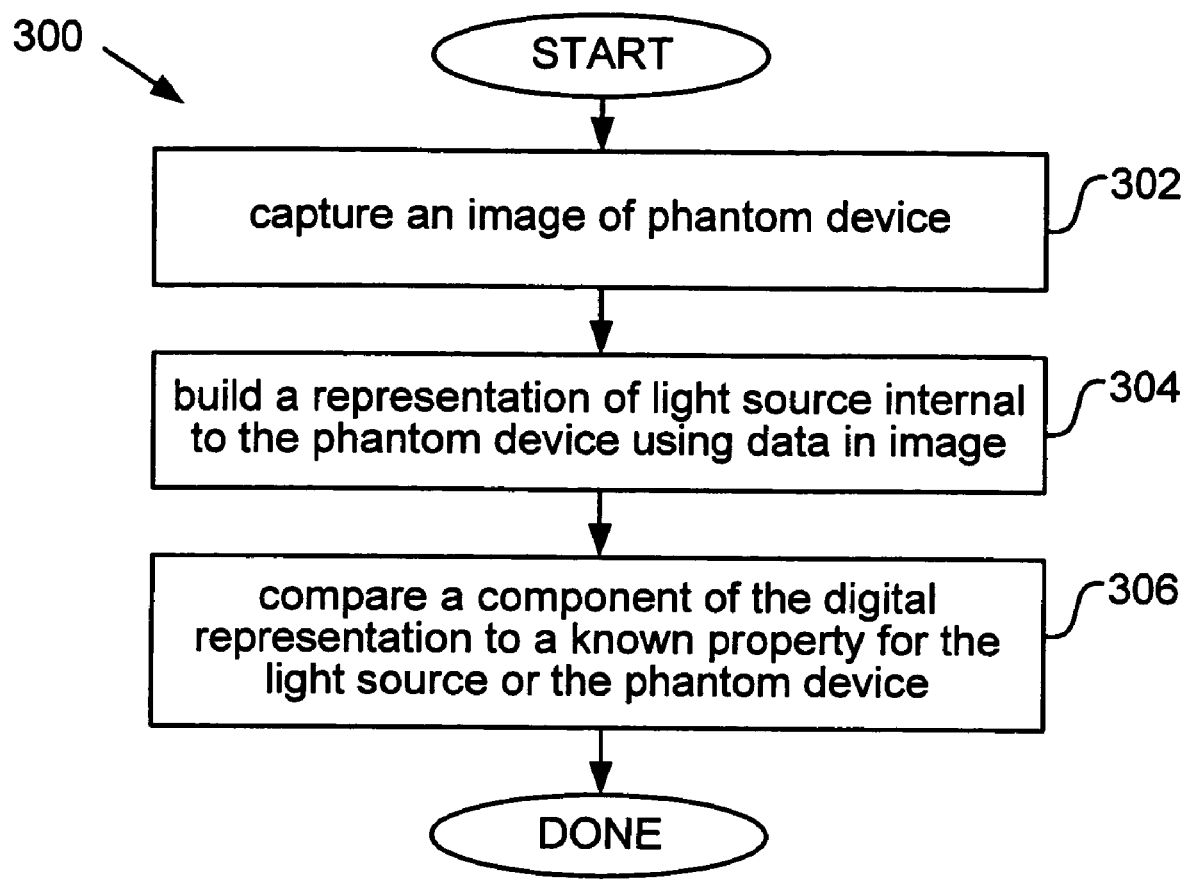
FIG. 3 illustrates a process flow for using a low-level light imaging system in accordance with one embodiment of the present invention.

FIG. 3 illustrates a process flow 300 for using a low-level light imaging system in accordance with one embodiment of the present invention. Process flow 300 assesses the performance of a low-level light imaging system by processing light output by a test device and quantitatively comparing a digital representation of the test device or a light source inside the phantom device against one or more known emission properties or characteristics for the phantom device or light source.

Process flow 300 begins by capturing an image of at least a portion of a phantom device 70 disposed in a field of view for a camera included in the low-level light imaging system (302). The phantom device comprises a body including an optically selective material designed to at least partially resemble the optical behavior of mammalian tissue. Typically, a user has places the test device in the imaging box and within the field of view of the camera. The user may then capture an image of the entire phantom device or a portion of interest that been zoomed in on.

The user may initiate software run by the imaging system that controls components of the imaging system responsible for image capture. The software may also automatically implement various digital reconstruction and comparison steps described below (304 and 306). For example, the user may launch imaging and acquisition software on a computer associated with the imaging system that initializes the camera and carries out imaging and assessment automatically. According to stored instructions, the software may automatically select a desired stage position if a moveable stage is used, prepare the system for photographic or luminescent image capture (e.g., turn on/off lights in the box), focus a lens, selectively position an appropriate lens filter, set an f-stop, transfer and store the image data, build a reconstruction, and compare the reconstruction results to known properties for the phantom device.

Image capture may include photographic and/or luminescent image capture. For luminescent image capture, software activates the camera to detect photons emitted from the phantom device, which usually corresponds to absolute units from the surface. The camera may capture the luminescence image over a set period of time (up to several minutes). A photon signal produced by the camera is transferred to the image processing unit 26 and/or computer 28 and used to construct a luminescent image of photon emission. A luminescence image records luminescence as a function of position. The luminescent image is captured without using light sources other than the luminescence from the sample itself. A photographic image may also be taken of the same sample to aid in position visualization of the luminescent data. One approach to generating such composite photographic/luminescence images is described in U.S. Pat. No. 5,650,135 issued to Contag et al. on Jul. 22, 1997. The entire disclosure of that patent is incorporated herein by reference for all purposes.

The image processing system then builds a 2-D or 3-D digital representation of a light source internal to the phantom device using data included in the image and a computer-implemented reconstruction model (304). In the case where scattering is large compared with absorption, such as red to near-infrared light passing through tissue or a phantom device that comprises an optically selective material configured to resemble tissue, the transport of light within the sample may be described by diffusion theory. In this case, the computer-implemented reconstruction model implements a diffusion model to build the light source digital representation. One 3-D diffusion software implementation reconstructs light data internal to the phantom device surface based on the surface light image data. In this case, the image and surface light data is converted into photon density just below the phantom device surface, and this photon density is used to produce 3-D light data internal to the test device surface including the light source. A suitable example of software that builds a 3-D digital representation of a light source internal to a test device using data from one or more images is described in commonly owned and pending patent application Ser. No. 10/606,976. Other software algorithms that build a 3-D digital representation of a light source using a diffuse tomography assessment are also suitable for use with the present invention.

Building the digital representation for the light source may rely on assumptions or estimates of optical properties for the phantom device. For example, reconstructing the digital representation of the light source may employ an optical scattering representation for the optically selective material used in the phantom device and employ an optical absorption representation for the optically selective material at one or more wavelengths. These representations for the phantom device are stored in memory and provided to the reconstruction algorithm when needed.

The resulting digital representation of the light source may include information that includes mathematical descriptions of: an estimated intensity of the light source, an estimated location of the light source within the phantom device, and/or an estimated size or shape of the light source. In one embodiment, the light source is reconstructed as a point. This expedites reconstruction and provides a simpler representation for the light source that includes flux and depth. A user may then readily read how deep and how strong the light source is within the test device. In another embodiment, the light source is reconstructed as a complex source characterized spatially in three dimensions. This reconstruction uses surface topography of the phantom device and produces a light source with 3-D information such as size and shape.

The image processing system then compares a component of the digital representation to a known property for the light source or the phantom device 70 (306). The known property for the light source may comprise any optical or spatial characteristic that describes the light source. In some cases, the known property for the light source may comprise: an intensity for the light source, a size or shape of the light source, and/or a spectral pattern for the light source. The known property for the phantom device may comprise any optical or spatial characteristic that describes the phantom device. The known property for the phantom device may comprise: scattering properties for the optically selective material, a surface size for a surface of the phantom device, a location of the light source within the test device or relative to a fiducial mark disposed on the test device, and an absorption response for the optically selective material (e.g., a spectral absorption response at one or more frequencies). Process flow 300 presumes that optical properties—such—as scattering and absorption coefficients—for the phantom device are known in advance. For example, a manufacturer of the phantom device may measure the optical properties before providing the phantom device to a customer or user. The manufacturer may also characterize the light source intensity and spectrum in advance and facilitate comparison.

A second image of the phantom device may also be captured at another wavelength. Since the optically selective material in the phantom device will absorb different wavelengths from the light source to various degrees, images taken at a second wavelength will produce an image with a different light output for the phantom device. This second image may then be processed to further assess the imaging software and provide more information for reconstruction and system assessment.

Process flow 300 thus benchmarks—or compares—calculated values output by software against known results the phantom device. For example, the comparison may reconstruct the 3-D position of the light source relative to a known position of the light source in the phantom device body (e.g., known from manufacturing) and then check the position of the light source generated in the reconstruction against the known location relative to the fiducial mark. Alternatively, the comparison may assess the reconstructed light source strength with the known strength.

Based on the comparison, the software may alter a parameter used in building the digital representation to increase reconstruction accuracy. For example, the optical scattering or optical absorption representation used in reconstructing the digital representation may be altered to attain a more accurate reconstruction. Other parameters used in the reconstruction, such as the resolution of the surface mesh, size of internal voxels, or the number of different wavelengths, can also be altered to affect the reconstruction. After the alteration, the image processing system may build a second digital representation of the light source using the altered parameter and the original image. Another comparison may ensue based on the second reconstruction. By imaging a test device whose performance according to a functioning imaging system is known, and altering one or more parameters used in reconstructing the digital representation, process flow 300 eventually produces validated software for the imaging system.

The present invention is independent of how testing is specifically performed in the imaging system or what tools are digitally used. While digital cameras output raw image data in "analog-to-digital convertor units" (ADU) or "counts", the terms are substantially equivalent for calibration purposes herein. Counts are uncalibrated units that refer to the amplitude of the signal detected by the digitizer incorporated into the CCD camera. The number of counts detected by the digitizer is proportional to the number of photons incident on a given CCD pixel. A distinction between absolute physical units and relative units of "counts" is that the radiance units refer to light emission from the animal or phantom device itself, as opposed to counts which refers to light emission incident on the detector. The use of real physical units (radiance) in a diffuse tomographic reconstruction allows the source intensity to be reconstructed in real physical units of flux or photons/sec.

Testing according to process flow 300 may be flexibly applied. In some cases, a manufacturer performs process flow 300 once during system set-up. Alternatively, process flow 300 may be repeated periodically during the operational life of the imaging system to verify the operational integrity of the software or system over time.

Figure 4:
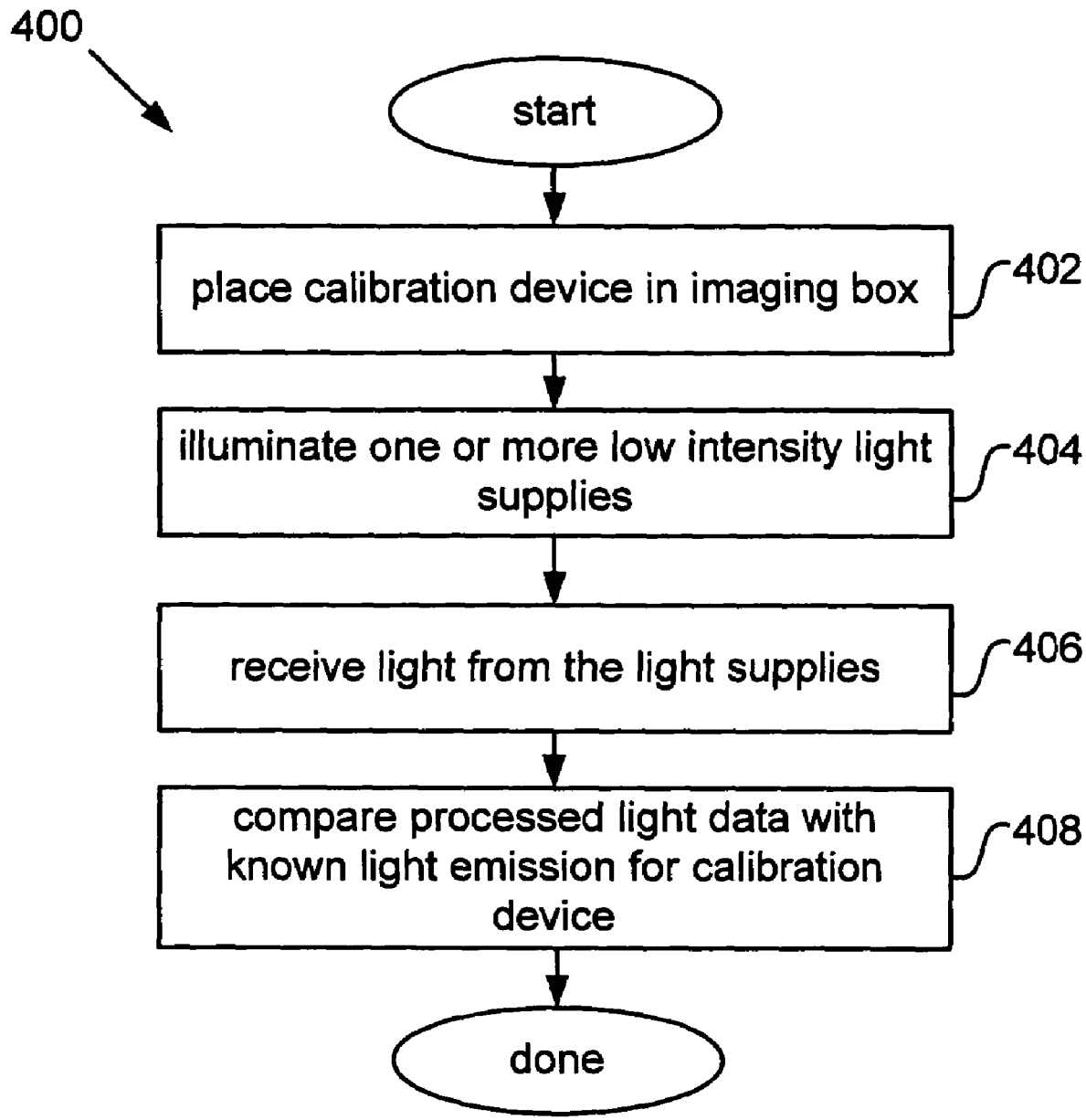
FIG. 4 illustrates a process flow for calibrating a low-level light imaging system in accordance with one embodiment of the present invention.

Process flow 300 assumes absolute calibration of the imaging system that converts counts to photons/sec/cm^2/steradian. This permits 3D reconstruction and derivation of light source strength in absolution units of flux (photons/sec). Depending on an application, light source strength can then be turned into more useful information. For example, light source strength can be turned into a number of luminescent cells provided the flux per cell is known. FIG. 4 illustrates a process flow 400 for calibrating a low-level light imaging system in accordance with one embodiment of the present invention.

Process flow 400 begins by placing a light calibration device in an imaging box (402). The light calibration device includes an array of low intensity light supplies of known intensity. Each low intensity light supply may be illuminated using a suitable electrical switch in conjunction with a light source operably coupled to one or more of the low intensity light supplies (404). One suitable device is described in commonly owned U.S. patent application Ser. No. 10/068,573, filed Feb. 6, 2002 and titled "Light Calibration Device for Use in Low Level Light Imaging Systems," which was incorporated by reference above.

A camera receives the light emitted from the calibration device (406) and provides a signal representative of the emitted light to an associated image processing system. This may include photographic and/or luminescent image capture. In one embodiment, the calibration device is used to assess the ability of the imaging box to seal light. In this case, light is received and processed from the low intensity light supplies for an extended period of time, long enough to assess the light integrity of the imaging box.

The image processing system processes the light emission data and compares the processed light data with known light emission for calibration device (408). In one embodiment, processing the light emitted from the calibration device comprises integrating the amount of light in photons received over time. Since the calibration device may be designed to emit a known value for light per unit time produced from each light supply, a comparison of the number of photons received by the imaging system with the number of photons produced from the calibration device gives a user a simple comparison for assessing accuracy for the imaging system. In one embodiment, the light sources are calibrated to absolute units, e.g., against a known radiance standard. For example, the light sources may be calibrated to a National Institute for Standards and Technology (NIST) traceable OL Series 425 Integrating Sphere available from Optronic Laboratories of Orlando, Fla.

The present invention may be used for a wide variety of imaging systems and applications. The present invention finds use with systems that employ any non-invasive methods and compositions for detecting, localizing and tracking light-emitting entities and biological events in a mammalian subject. For example, the imaging system 10 of FIG. 1 and phantom device 70 may be implemented with intensified Charge-Coupled Device (CCD) cameras to detect the localization of light-producing cells (e.g., certain bacteria or tumor cells made bioluminescent by transforming them with luciferase DNA constructs) inside of living animals, such as mice. In such applications, an animal containing the bioluminescent cells is placed inside of the specimen chamber, and within the field of view for a photodetection device, such as an intensified CCD camera.

In addition, embodiments of the present invention may relate to computer readable medium and computer storage products with a computer-readable medium that has computer code thereon for performing various computer-implemented operations described herein. The media and computer code may be those specially designed and constructed for the purposes of the present invention, or they may be of the kind well known and available to those having skill in the computer software arts. Examples of computer-readable media include, but are not limited to: magnetic media such as hard disks, optical media such as CD-ROMs; and hardware devices that are specially configured to store and execute program code, such as programmable logic devices (PLDs) and ROM and RAM devices. Examples of computer code include machine code, such as produced by a compiler, and files containing higher level code that are executed by a computer using an interpreter.

While this invention has been described in terms of several preferred embodiments, there are alterations, permutations, and equivalents which fall within the scope of this invention which have been omitted for brevity's sake. For example, although the present invention has primarily been discussed with respect to luminescent and fluorescent light imaging, phantom devices as described herein are also well-suited for use with other wavelength ranges and imaging modalities, such as near IR. It is therefore intended that the scope of the invention should be determined with reference to the appended claims.

What is claimed is:

1. A phantom device for use with a low-level light imaging system, the phantom device comprising:
   a body including one or more surfaces and an optically selective material designed to at least partially resemble the optical behavior of mammalian tissue; and
   a low intensity light source disposed within the body and configured to emit light from within the body, through the optically selective material and to the one or more surfaces,
   wherein the light source is configured to emit a photon flux in the range of about $10^4$ to about $10^{13}$ photons/second.

2. The device of claim 1 wherein the optically selective material is designed or configured to resemble an optical absorption property of mammalian tissue.

3. The device of claim 1 wherein the optically selective material is designed or configured to resemble an optical scattering property of mammalian tissue.

4. The device of claim 1 wherein the optically selective material is substantially homogeneous.

5. The device of claim 1 wherein the low intensity light source comprises a radiation source configured to produce electrons that strike a light-emitting surface.

6. The device of claim 5 wherein the low intensity radiation light source is embedded in an end of a rod that comprises the optically selective material.

7. The device of claim 1 wherein the low intensity light source comprises an optical fiber having a first end configured to receive light from a light supply and a second end within the body.

8. The device of claim 7 further comprising a hole that receives a rod that includes a channel configured to receive the optical fiber and extending from a first end of the rod disposed proximate to the light supply to a second end of the rod within the body.

9. The device of claim 8 wherein the rod comprises the optically selective material.

10. The device of claim 7 wherein the light source comprises a light emitting diode that is configured to illuminate the first end of the optical fiber.

11. The device of claim 10 further comprising a second light emitting diode that is configured to illuminate the first end of the optical fiber, wherein the first and second light emitting diodes resemble a light spectrum for a biological reporter.

12. The device of claim 10 wherein the light emitting diode receives current from a current regulating source.

13. The device of claim 1 wherein a height for the body is designed to resemble a height of a mammal to be imaged.

14. The device of claim 13 wherein surface topography of the body is designed to match the surface topography of the mammal.

15. The device of claim 13 wherein the surface shape resembles a trapezoid.

16. The device of claim 13 wherein the light source emits light in the range of about 400 nanometers to about 1300 nanometers.

17. The device of claim 1 wherein the low intensity light source emits a photon flux in the range of about $10^4$ to about $10^{10}$ photons/second.

18. The device of claim 1 wherein the low intensity light source emits light from about $10^{-15}$ to $10^{-6}$ watts of light.

19. The device of claim 1 wherein light radiance from the surface of the phantom device is from about $10^3$ to about $10^{11}$ photons/second/centimeter squared/steradian.

20. The device of claim 1 wherein the low intensity light source emits a light spectrum that is substantially similar to a biological reporter.

21. The device of claim 20 wherein the optically selective material comprises titanium dioxide.

22. The device of claim 1 wherein the body is heterogeneous and includes at least two different materials.

23. A phantom device for testing a low-level light imaging system, the device comprising:
   a body including one or more surfaces and a substantially homogeneous and optically selective material designed to at least partially resemble the optical behavior of mammalian tissue, wherein the body includes a shape that resembles a mammal to be imaged and wherein a height for the body is designed to resemble a height of the mammal; and
   a low intensity light source disposed within the body and configured to emit light from within the body, through the optically selective material and to the one or more surfaces.

24. The device of claim 23 wherein the optically selective material is configured to resemble an optical absorption property of mammalian tissue.

25. The device of claim 24 wherein the optically selective material comprises a reddish dye.

26. The device of claim 23 wherein the optically selective material is configured to resemble an optical scattering property of mammalian tissue.

27. The device of claim 26 wherein the optically selective material comprises a scattering particle.

28. The device of claim 25 wherein the low intensity light source emits light between about 1 nanowatt and about 10 nanowatts of light.

29. A method for testing a low-level light imaging system, the method comprising:
   capturing an image of at least a portion of a phantom device disposed in a field of view for a camera included in the low-level light imaging system, the phantom device comprising a body including an optically selective material designed to at least partially resemble the optical behavior of mammalian tissue;
   building a digital representation of a light source internal to the phantom device using data included in the image; and
   comparing a component of the digital representation to a known property for the light source or the phantom device.

30. The method of claim 29 wherein the known property for the light source comprises one of: intensity for the light source, a size of the light source, and a spectral pattern for the light source.

31. The method of claim 29 wherein the known property for the phantom device comprises one of: a surface size for a surface of the phantom device, a location of the light source within the phantom device, and a spectral response for the optically selective material.

32. The method of claim 29 wherein the component comprises one of: a flux from a surface of the phantom device, an estimated intensity of the light source, an estimated location of the light source within the phantom device, and an estimated size of the light source.

33. The method of claim 29 wherein the light source is reconstructed as a point.

34. The method of claim 29 wherein the light source is reconstructed as a complex source characterized spatially in three dimensions.

35. The method of claim 29 wherein reconstructing the digital representation of the light source employs one of: an optical scattering representation for the optically selective material and an optical absorption representation for the optically selective material.

36. The method of claim 29 wherein building a digital representation comprises a diffuse tomography assessment for the light source that is stored in software run with the imaging system.

37. The method of claim 29 further comprising capturing a second image of the phantom device at a different wavelength.

38. The method of claim 29 further comprising:
   altering a parameter used in reconstructing the digital representation; and
   reconstructing a second digital representation using the altered parameter and the data included in the image.

39. The method of claim 29 further comprising assessing performance of the low-level light imaging system using the digital representation of the light source.

40. The method of claim 29 wherein the image comprises one of a photographic or a luminescent image.

41. The method of claim 29 further comprising calibrating the low-level light imaging system against a known intensity light source.

42. The method of claim 29 wherein the light source emits fluorescent light.

43. A method for testing a low-level light imaging system, the method comprising:
   calibrating the low-level light imaging system against a known intensity light source;
   capturing an image of at least a portion of a phantom device disposed in a field of view for a camera included in the low-level light imaging system;
   building a digital representation of a light source internal to the phantom device using data included in the image; and
   comparing a component of the digital representation to a known property for the light source or the phantom device.

44. A computer readable medium including instructions for testing a low-level light imaging system, the instructions comprising:
   instructions for capturing an image of at least a portion of a phantom device disposed in a field of view for a camera included in the low-level light imaging system, the phantom device comprising a body including an optically selective material designed to at least partially resemble the optical behavior of mammalian tissue;

instructions for reconstructing a digital representation of the light source internal to the phantom device using data included in the image; and instructions for comparing a component of the digital representation to a known property for the light source or the phantom device.

45. The computer readable medium of claim 44 wherein the known property for the light source comprises one of: intensity for the light source, a size of the light source, and a spectral pattern for the light source.

46. The computer readable medium of claim 44 wherein the known property for the phantom device comprises one of: a surface size for a surface of the phantom device, a location of the light source within the phantom device, and a spectral response for the optically selective material.

47. The computer readable medium of claim 44 wherein the image comprises a luminescent image.

* * * * *

UNITED STATES PATENT AND TRADEMARK OFFICE
CERTIFICATE OF CORRECTION

| | |
|---|---|
| PATENT NO. | : 7,629,573 B2 |
| APPLICATION NO. | : 10/997324 |
| DATED | : December 8, 2009 |
| INVENTOR(S) | : Bradley W. Rice et al. |

It is certified that error appears in the above-identified patent and that said Letters Patent is hereby corrected as shown below:

On the Title Page

--Related U.S. Application Data should read as follows:

item --(63) Continuation-in-Part of application No. 10/068,573, filed Feb. 6, 2002, now Patent No. 6,919,919.--

Signed and Sealed this

Eighth Day of June, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,629,573 B2 | Page 1 of 1 |
| APPLICATION NO. | : 10/997324 | |
| DATED | : December 8, 2009 | |
| INVENTOR(S) | : Rice et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1414 days.

Signed and Sealed this

Second Day of November, 2010

David J. Kappos
*Director of the United States Patent and Trademark Office*